United States Patent
Moon et al.

(10) Patent No.: US 9,403,912 B2
(45) Date of Patent: Aug. 2, 2016

(54) ANTI-ERBB2 ANTIBODY VARIANTS

(71) Applicant: CHONG KUN DANG PHARMACEUTICAL CORP., Seoul (KR)

(72) Inventors: Seung-Kee Moon, Yongin-si (KR); So-Ra Park, Yongin-si (KR); Ki-Young An, Yongin-si (KR)

(73) Assignee: CHONG KUN DANG PHARMACEUTICAL CORP., Seoul (KR)

( * ) Notice: Subject to any disclaimer, the term of this patent is extended or adjusted under 35 U.S.C. 154(b) by 0 days.

(21) Appl. No.: 14/399,265

(22) PCT Filed: Apr. 26, 2013

(86) PCT No.: PCT/KR2013/003635
§ 371 (c)(1),
(2) Date: Nov. 6, 2014

(87) PCT Pub. No.: WO2013/168918
PCT Pub. Date: Nov. 14, 2013

(65) Prior Publication Data
US 2015/0104443 A1    Apr. 16, 2015

(30) Foreign Application Priority Data
May 8, 2012   (KR) .................. 10-2012-0048805

(51) Int. Cl.
*C07K 16/32*   (2006.01)
(52) U.S. Cl.
CPC ............. *C07K 16/32* (2013.01); *C07K 2317/24* (2013.01); *C07K 2317/56* (2013.01); *C07K 2317/73* (2013.01); *C07K 2317/92* (2013.01)

(58) Field of Classification Search
CPC . C07K 16/32; C07K 2317/56; C07K 2317/24
USPC ................... 424/133.1; 530/387.3; 536/23.53
See application file for complete search history.

(56) References Cited

U.S. PATENT DOCUMENTS

| | | | |
|---|---|---|---|
| 2004/0018573 A1 | 1/2004 | Power et al. | |
| 2007/0202552 A1* | 8/2007 | Sidhu ................... | C07K 16/005 435/7.23 |
| 2007/0237764 A1* | 10/2007 | Birtalan ........... | C07K 14/70503 424/133.1 |
| 2008/0085277 A1 | 4/2008 | Cho et al. | |
| 2010/0158926 A1 | 6/2010 | Cartilage et al. | |
| 2011/0159014 A1 | 6/2011 | Lowman et al. | |

FOREIGN PATENT DOCUMENTS

| | | | |
|---|---|---|---|
| EP | 2112167 A2 | 10/2009 | |
| WO | WO 2004/003019 | * | 6/2004 |

OTHER PUBLICATIONS

Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
International Search Report for International Application No. PCT/KR2013/003635, mailed Aug. 20, 2013 (6 pages).

* cited by examiner

*Primary Examiner* — Lynn Bristol
(74) *Attorney, Agent, or Firm* — Clark & Elbing LLP; Susan M. Michaud

(57) ABSTRACT

The present invention relates to anti-ErbB2 antibody variants or antigen-binding fragments thereof, nucleic acid molecules encoding them, and their uses. The antibody variants of the present invention are capable of binding to ErbB2 with high affinity. Therefore, the antibody variants are ability to effectively prevent or treat various cancers with a low amount.

6 Claims, 6 Drawing Sheets

Fig. 3

```
SEQ ID NO:1   EVQLVESGGGLVQPGGSLRLSCAASGFNIKDTYIHWVRQAPGKGLEWVARIYPTNGYTRY   60
SEQ ID NO:3   EVQLVESGGGLVQPGGSLRLSCAASGFNIKDTYIHWVRQAPGKGLEWVARIYPTNGYTRY   60
              ADSVKGRFTISADTSKNTAYLQMNSLRAEDTAVYYCSRWGGDGFYAMDYWGQGTLVTVSS  120
              ADSVKGRFTISADTSKNTAYLQMNSLRAEDTAVYYCSRWGG GFYA  WGQGTLVTVSS  120
              ADSVKGRFTISADTSKNTAYLQMNSLRAEDTAVYYCSRWGGWGFYAFALWGQGTLVTVSS  120

SEQ ID NO:1   EVQLVESGGGLVQPGGSLRLSCAASGFNIKDTYIHWVRQAPGKGLEWVARIYPTNGYTRY   60
SEQ ID NO:4   EVQLVESGGGLVQPGGSLRLSCAASGFNIKDTYIHWVRQAPGKGLEWVARIYPTNGYTRY   60
              ADSVKGRFTISADTSKNTAYLQMNSLRAEDTAVYYCSRWGGDGFYAMDYWGQGTLVTVSS  120
              ADSVKGRFTISADTSKNTAYLQMNSLRAEDTAVYYCSRW    GFY+  +WGQGTLVTVSS  120
              ADSVKGRFTISADTSKNTAYLQMNSLRAEDTAVYYCSRWNAKGFYSFVHWGQGTLVTVSS  120

SEQ ID NO:1   EVQLVESGGGLVQPGGSLRLSCAASGFNIKDTYIHWVRQAPGKGLEWVARIYPTNGYTRY   60
SEQ ID NO:6   EVQLVESGGGLVQPGGSLRLSCAASGFNIKDTYIHWVRQARGKGLEWVARIYPTNGYTRY   60
              ADSVKGRFTISADTSKNTAYLQMNSLRAEDTAVYYCSRWGGDGFYAMDYWGQGTLVTVSS  120
              ADSVKGRFTISADTSKNTAYLQMNSLRAEDTAVYYCSRWGG GFYA  WGQGTLVTVSS  120
              ADSVKGRFTISADTSKNTAYLQMNSLRAEDTAVYYCSRWGGWGFYAFALWGQGTLVTVSS  120
```

Fig. 4

```
SEQ ID NO:2  DIQMTQSPSSLSASVGDRVTITCRASQDVNTAVAWYQQKPGKAPKLLIYSASFLYSGVPS 60
SEQ ID NO:5  DIQMTQSPSSLSASVGDRVTITCRASQDVNTAVAWYQQKPGKAPKLLIYSASFLYSGVPS 60
             DIQMTQSPSSLSASVGDRVTITCRASQDVNTAVAWYQQKPGKAPKLLIYSASFLYSGVPS

RFSGSRSGTDFTLTISSLQPEDFATYYCQQHYTTPPTFGQGTKVEIK 107
             RFSGSRSGTDFTLTISSLQPEDFATYYCQQHY TP +FGQGTKVEIK
             RFSGSRSGTDFTLTISSLQPEDFATYYCQQHYQTPASFGQGTKVEIK 107

SEQ ID NO:2  DIQMTQSPSSLSASVGDRVTITCRASQDVNTAVAWYQQKPGKAPKLLIYSASFLYSGVPS 60
SEQ ID NO:7  DIQMTQSPSSLSASVGDRVTITCRASQDVNTAVAWYQQKPGKAPKLLIYTTTWPYSGVPS 60
             DIQMTQSPSSLSASVGDRVTITCRASQDVNTAVAWYQQKPGKAPKLLIY+  ++ YSGVPS

RFSGSRSGTDFTLTISSLQPEDFATYYCQQHYTTPPTFGQGTKVEIK 107
             RFSGSRSGTDF+LTISSLQPEDFATYYCQQ+Y TP TFGQGTKVEIK
             RFSGSRSGTDFSLTISSLQPEDFATYYCQQYYNTPVTFGQGTKVEIK 107
```

H. 4D5
1. D98W
2. A091
3. AH06
4. A058
5. AH16

Fig. 7
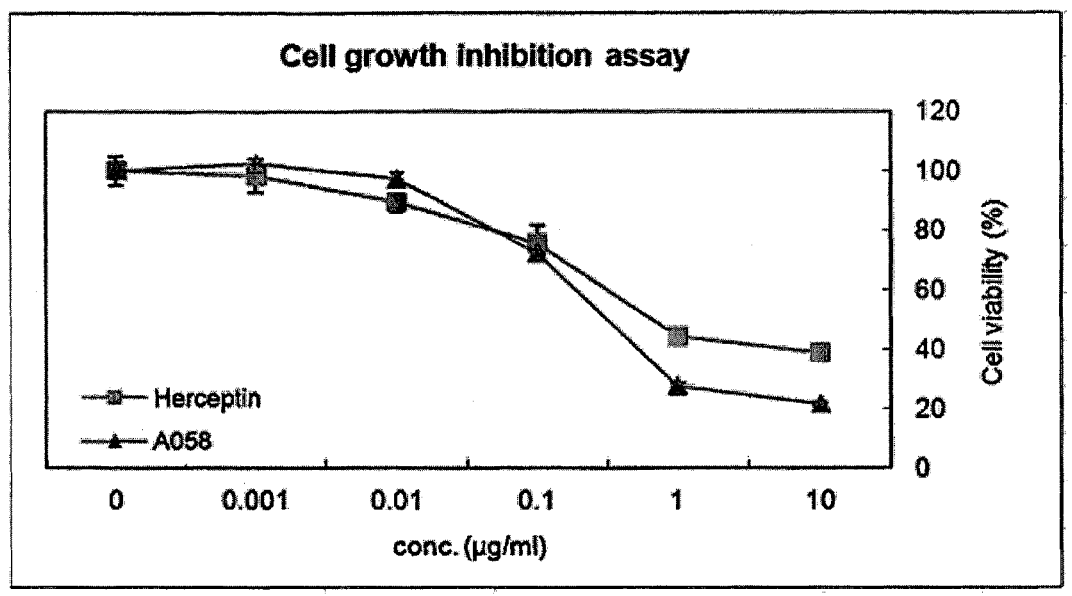
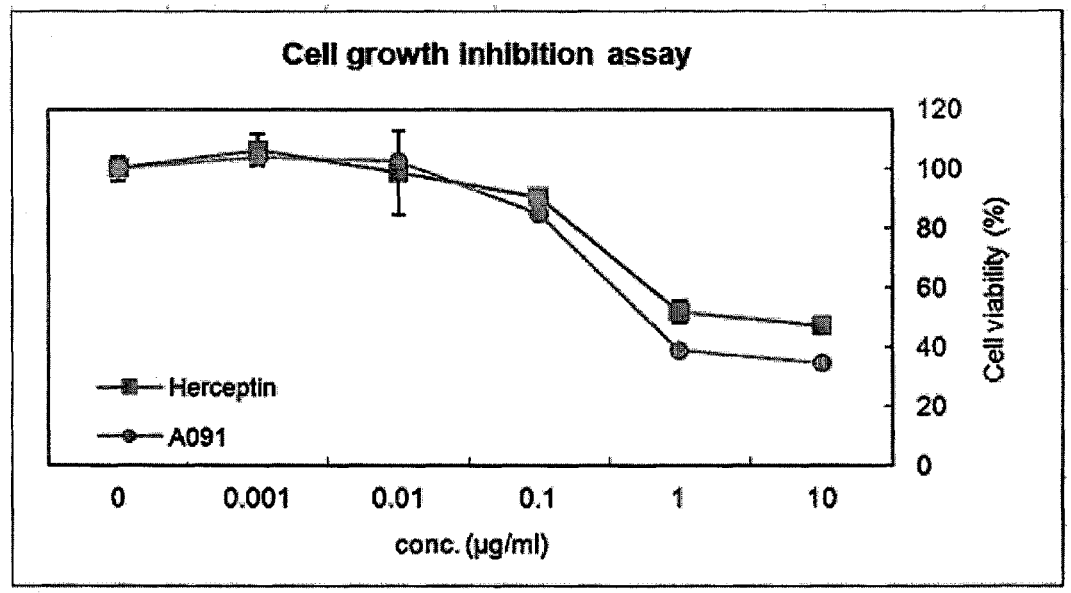

Fig. 8
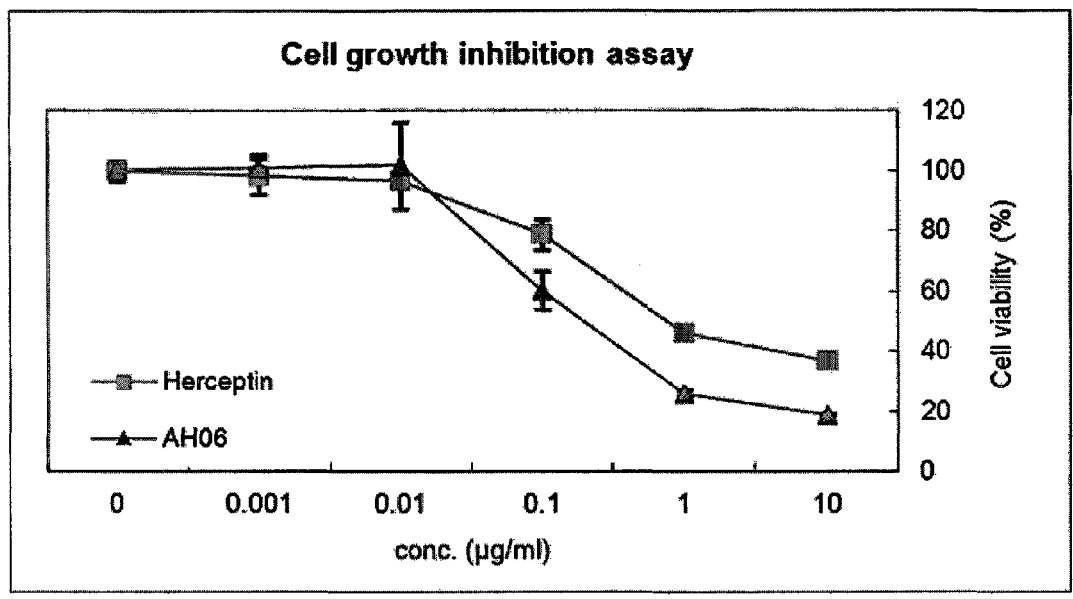
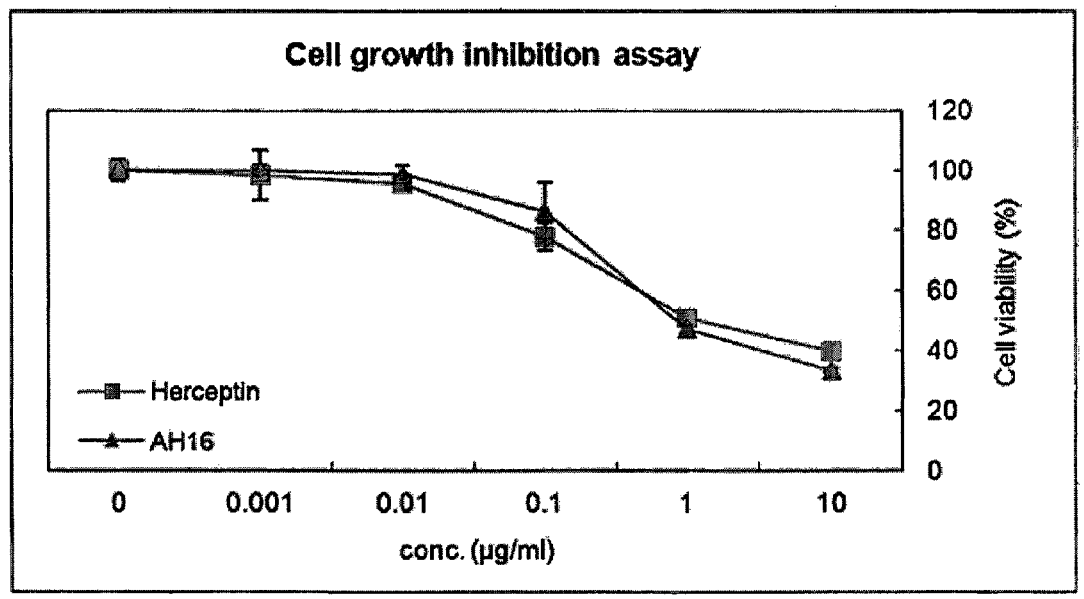

ANTI-ERBB2 ANTIBODY VARIANTS

CROSS-REFERENCE TO RELATED APPLICATIONS

This application is the U.S. National Phase of International Patent Application No. PCT/KR2013/003635, filed Apr. 26, 2013, which claims the benefit of Korean Patent Application No. 2012-0048805, filed May 8, 2012, the entire contents of which are incorporated by reference herein.

BACKGROUND OF THE INVENTION

1. Field of the Invention

The present invention relates to anti-ErbB2 antibody variants or antigen-binding fragments thereof, nucleic acid molecules encoding them, and their uses.

2. Description of the Related Art

There has been reported that HER2 (ErbB2), which is a member of receptor tyrosin kinases such as EGFR (ErbB1), HER3 (ErbB3) and HER4 (ErbB4), locates on a cell membrane, and plays an important role in cell growth, differentiation and survival (Jaclyn et al. *Clin Breast Cancer.* 8:38-49 (2008)). There has been also reported that unlike the other HER family proteins, HER2 is not activated dependant on a ligand, and that approximately 20,000 of HER2 is expressed on a cell membrane of normal cells while approximately 20,000,000 of HER2 is expressed on a cell membrane of cancer cells (Shepard et al. *J Clin Immunol.* 11:117-127 (1991)). This HER2 overexpression induces many heterodimers between HER2 and HER1, or HER2 and HER3 as well as HER2-HER2 homodimers, thereby inducing cell proliferation and growth, resulting in acceleration in a transformation into cancer cells (Mayumi et al. *Clin Cancer Res.* 12:7242-7251 (2006)).

Until now, the overexpression of HER2 was detected in various cancers such as breast cancer (25-30%), ovarian cancer (15-30%), gastric cancer (23%), lung cancer (11-32%), renal cell carcinoma (30-40%), rectal cancer (17-90%), pancreatic cancer (26-45%), bladder cancer (44%), prostate cancer (12%), and head and neck cancer (29-39%) (*Cancer Immunol Immunother* 53:166-175 (2004); *Clin Cancer Res* 12:4377s-4383s (2006); *Br J Cancer* 91:1195-1199 (2004); *Cancer* 94:2584-2589 (2002); *Cancer* 98: 66-73 (2003); *Int J Oncol* 27: 681-685 (2005); *Int J Pancreatol* 17:15-21 (1995); *Int J Cancer* 87:349-359 (2000); *Ann Oncol* 12:S15-S19 (2001); *J Pathol* 204:317-325 (2004)). Furthermore, the overexpression of HER2 was observed in endometrial cancer, salivary gland tumor, colon cancer and thyroid cancer (*Science* 229:974 (1985); *Lancet.* 1:765-767 (1986); *Mol Cell Biol.* 6:955-958 (1986); *Oncogene Res.* 3:21-31 (1988); *Oncogene* 4:81-88 (1989); *Cancer Res.* 51:1034 (1991); *Gynecol. Oncol,* 38:364 (1990); *Cancer Res.* 50:421-425 (1990); *Cancer Res.* 50:5184 (1990); *Cancer Res.* 49:6605 (1989); *Mol. Carcinog.* 3:254-257 (1990); *Br, J. Cancer* 57:358-363 (1988); *Pathobiology* 59:46-52 (1991); *Cancer* 65:88-92 (1990)).

Herceptin (Trastuzumab, 4D5) which is an sole anticancer drug targeting HER2 received marketing approval in 1998 for the treatment of patients with metastatic breast cancer or early breast cancer whose tumors overexpress the HER2 protein, and is administered to the patient in combination with the other anticancer drugs (*J. Clin. Oncol.* 17:2639-2264 (1999)). Herceptin inhibits survival and proliferation of cancer cells by inhibiting the formation of HER2-HER2 homodimer (*Ann Oncol* 18:977-984 (2007)).

However, although Herceptin was succeeded in HER2-targeting anticancer drug, it merely exhibited response effect of 12-34% when administered solely and response effect of 38-50% when coadministered. In addition, where Herceptin was administered to patients solely or in combination with the other drugs, abnormal heart diseases were developed in 2-7% or 11-28% of the patients, and one woman among ten women could not receive the administration of Herceptin due to the risk of developing heart diseases (*N Engl J Med* 357:39-51 (2007)). Hence, there is a strong demand for an antibody whose side effects are less than Herceptin, and thus Omnitarg (Genetech) is undergoing phase III clinical trial (*Clin Cancer Res* 12:4436s-4440s (2006)). However, Omnitarg has a problem with lower efficacy as compared with Herceptin. Accordingly, it is required to develop a novel anti-HER2 antibody or improved form of which, for example 4D5 variants having improved affinity, efficacy or the like.

Generally, it is difficult to prepare an antibody with high affinity for antigen since an exposed surface of the antigen is limited. Especially, when the in vitro selection is performed from a naïve phage display library, this phenomenon more occurs. Accordingly, the affinity of antibodies prepared from the naïve phage display library is mere 10-100 nM (Iwai et al. *Protein Eng Des Set.* 23:185-193 (2010)).

Strategies for enhancing the affinity of antibodies are divided into a random approach and a targeted approach (Sheedy et al. *Biotechnol Adv.* 5(4):333-52 (2007)). The targeted approach is concerned with a strategy to introduce some mutations into specific amino acids, e.g., CDR or FR, in which targeted PCR, CDR walking, site-directed mutagenesis and CDR target hotspot are used. The random approach is concerned with a strategy to introduce some modifications into variable domains, in which error-prone PCR, DNA shuffling and chain shuffling (Kim et al. *Adv Drug Deliv Rev.* 58:657-667 (2006)). Various variants prepared by the above-mentioned methods are constructed as libraries, followed by displaying the various variant libraries on phage surface, and then improved variants are selected. Besides, yeast display and ribosome display are also used for the display (Rader et al. *Curr Opin Biotechnol.* 8:503-508 (1997); Zahnd et al. *J Biol Chem.* 279(18):18870-18877 (2004)).

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made intensive researches to develop antibody variants having more improved affinity and cancer cell-inhibitory activity than the anti-ErbB2 humanized antibody 4D5. As a result, we have prepared anti-ErbB2 antibody variants which can exhibit not only higher affinity but also higher cancer cell-inhibitory activity than the parent antibody.

Accordingly, it is an object of this invention to provide an anti-ErbB2 antibody variant or antigen-binding fragment thereof.

It is an additional object of this invention to provide a nucleic acid molecule encoding a heavy chain variable domain of the anti-ErbB2 antibody variant or antigen-binding fragment thereof.

It is another object of this invention to provide a nucleic acid molecule encoding a light chain variable domain of the anti-ErbB2 antibody variant or antigen-binding fragment thereof.

It is still another object of this invention to provide a pharmaceutical composition for preventing or treating a cancer.

It is still further another object of this invention to provide a method of preventing or treating a cancer.

Other objects and advantages of the present invention will become apparent from the detailed description to follow taken in conjugation with the appended claims and drawings.

BRIEF DESCRIPTION OF THE DRAWINGS

FIG. 3 represents compare results of amino acid sequences between $V_H$ of the humanized antibody 4D5 (SEQ ID NO:1), $V_H$ of AH06 and A058 (each SEQ ID NO:3), $V_H$ of AH16 (SEQ ID NO:4), and $V_H$ of A091 (SEQ ID NO:6).

FIG. 4 represents the compare results of amino acid sequences between $V_L$ of the humanized antibody 4D5, AH06 and AH16 (each SEQ ID NO:2), $V_L$ of A05 (SEQ ID NO:5), and $V_L$ of A091 (SEQ ID NO:7).

FIGS. 6-8 represent analysis results for inhibitory effects of the anti-ErbB2 antibody variant on cell proliferation. FIG. 6: D98W, FIG. 7: A058 and A091, FIG. 8: AH06 and AH16. Purified IgG was assessed in NCI-N87 cells for 6 days.

DETAILED DESCRIPTION OF THIS INVENTION

Figure 1:
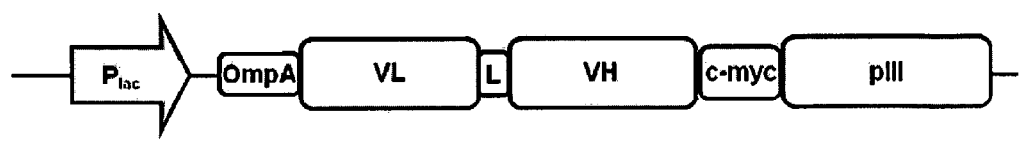
FIG. 1 schematically represents parts of a vector expressing transcripts for displaying scFv. An open reading frame encodes the OmpA signal sequence, a light chain variable domain ($V_L$), a linker sequence (L), a heavy chain variable domain ($V_H$), a c-myc tag sequence and a virus capsid protein.

In one aspect of the present invention, there is provided an anti-ErbB2 antibody variant or antigen-binding fragment thereof, comprising: (a) a light chain variable domain; and (b) a heavy chain variable domain which amino acid sequence has at least two amino acid substitutions selected from the group consisting of: a substitution of Pro at position 41 with Arg, a substitution of Gly at position 96 with Asn, a substitution of Gly at position 97 with Ala, a substitution of Asp at position 98 with Trp, a substitution of Asp at position 98 with Lys, a substitution of Ala at position 100b with Ser, a substitution of Met at position 100c with Phe, a substitution of Asp at position 101 with Ala, a substitution of Asp at position 101 with Val, a substitution of Tyr at position 102 with His, and a substitution of Tyr at position 102 with Leu, wherein the positions are indicative of positions on the amino acid sequence of SEQ ID NO:1, and numbered according to the Kabat numbering system.

The present inventors have made intensive researches to develop antibody variants having more improved affinity and cancer cell-inhibitory activity than the anti-ErbB2 humanized antibody 4D5. As a result, we have prepared anti-ErbB2 antibody variants which can exhibit not only higher affinity but also higher cancer cell-inhibitory activity than the parent antibody.

The present invention will be described hereinbelow in more detail.

I. Anti-ErbB2 Antibody Variants and Antigen-Binding Fragment Thereof

The antibody variants of this invention have a specific binding affinity to ErbB2.

The term "antibody variant" used herein refers to an amino acid-substituted variant having variable domains which are substituted with at least two amino acids in heavy and/or light chain variable domain of 4D5 antibody. The present invention provides antibody variants having improved affinity and cancer cell proliferation-inhibitory activity by amino acid substitutions at a specific position of heavy and/or light chain variable domain of the parent antibody 4D5.

As shown in Examples below, affinity of the present antibody variants for ErbB2 is improved by up to maximum 8-fold when compared with 4D5 (Table 5), and inhibitory activity of the present antibody variants to gastric cancer cell proliferation is about 3.5-fold higher than 4D5 (FIG. 8).

The heavy chain variable domain of 4D5 comprises the amino acid sequence of SEQ ID NO:1, and the light chain variable domain of 4D5 comprises the amino acid sequence of SEQ ID NO:2.

Antibody is meant to include the entire antibody as well as any antibody fragments.

The entire antibody includes two full-length light chains and two full-length heavy chains, and each light chain is linked to the heavy chain by disulfide bond. The heavy chain constant region includes five different isotypes (γ, μ, α, δ and ε) of which the subclass is classified into γ1, γ2, γ3, γ4, α1 and α2. The light chain constant region includes two different isotypes (κ and λ).

Antigen-binding fragment refers to any antibody fragment capable of binding antigen including Fab, F(ab'), F(ab')$_2$, Fv and so on. Fab has one antigen-binding site which is composed of one variable domain from each heavy and light chain of the antibody, one constant region of light chain and the first constant region ($CH_1$) of heavy chain. Fab' is different to Fab in the sense that there is a hinge region containing one or more cysteine residues at C-terminal of $CH_1$ domain of heavy chain. F(ab')$_2$ antibody is produced by forming a disulfide bond between cysteine residues of hinge region of Fab'. Fv is a minimal antibody fragment including one variable region from each heavy and light chain and recombinant technique to prepare a Fv fragment is disclosed in PCT WO 88/10649, WO 88/106630, WO 88/07085, WO 88/07086 and WO 88/09344. Two-chain Fv is linked by non-covalent bond between one variable region of each heavy and light chain, and single-chain Fv is generally linked by covalent bond via a peptide linker between one variable region of each heavy and light chain or is directly linked to each other at C-terminal, forming a dimer such as two-chain Fv. Such antibody fragments may be obtained using a proteolytic enzymes {e.g., a whole antibody is digested with papain to produce Fab fragments, and pepsin treatment results in the production of F(ab')$_2$ fragments), and may be prepared by genetic recombination techniques.

According to an embodiment, the antibody of this invention is a form of Fv or entire antibody. In addition, the heavy chain constant region is selected from the isotypes consisting of γ, μ, α, δ or ε. Preferably, the heavy chain constant region includes γ1 (IgG1), γ3 (IgG3) and γ4 (IgG4) isotype. The light chain constant region includes κ and λ isotype.

The term "heavy chain" used herein refers to both a full-length heavy chain and its part, which includes variable domain ($V_H$) containing the amino acid sequence with a variable region sequence for specifically binding to antigen and three constant domains ($C_{H1}$, $C_{H2}$ and $C_{H3}$). The term "light chain" used herein refers to both a full-length light chain and its part, which includes variable domain (V$_L$) containing the amino acid sequence with a variable region sequence for specifically binding to antigen and three constant domains (C$_L$).

According to an embodiment, the heavy chain variable domain comprises the following amino acid substitutions:

(i) a substitution of Asp at position 98 with Trp, a substitution of Met at position 100c with Phe, a substitution of Asp at position 101 with Ala, and a substitution of Tyr at position 102 with Leu (SEQ ID NO:3);

(ii) a substitution of Gly at position 96 with Asn, a substitution of Gly at position 97 with Ala, a substitution of Asp at position 98 with Lys, a substitution of Ala at position 100b with Ser, a substitution of Met at position 100c with Phe, a substitution of Asp at position 101 with Val, and a substitution of Tyr at position 102 with His (SEQ ID NO:4); or (iii) a substitution of Pro at position 41 with Arg, a substitution of Asp at position 98 with Trp, a substitution of Met at position 100c with Phe, a substitution of Asp at position 101 with Ala, and a substitution of Tyr at position 102 with Leu (SEQ ID NO:6).

The positions are indicative of positions on amino acid sequence of SEQ ID NO:1, and are numbered according to the Kabat numbering system. Specifically, the position 41 according to the Kabat numbering system means a 41th amino acid of SEQ ID NO:1 (Pro), the position 96 according to the Kabat numbering system means a 100th amino acid of SEQ ID NO:1 (Gly), the position 97 according to the Kabat numbering system means a 101th amino acid of SEQ ID NO:1 (Gly), the position 98 according to the Kabat numbering system means a 102th amino acid of SEQ ID NO:1 (Asp), the position 100b according to the Kabat numbering system means a 106th amino acid of SEQ ID NO:1 (Ala), the position 100c according to the Kabat numbering system means a 107th amino acid of SEQ ID NO:1 (Met), the position 101 according to the Kabat numbering system means a 108th amino acid of SEQ ID NO:1 (Asp), and the position 102 according to the Kabat numbering system means a 109th amino acid of SEQ ID NO:1 (Tyr).

According to an embodiment, the light chain variable domain comprises the amino acid sequence of SEQ ID NO:2 or at least two amino acid substitutions selected from the group consisting of: a substitution of Ser at position 50 of SEQ ID NO:2 with Thr, a substitution of Ala at position 51 of SEQ ID NO:2 with Thr, a substitution of Ser at position 52 of SEQ ID NO:2 with Thr, a substitution of Phe at position 53 of SEQ ID NO:2 with Trp, a substitution of Leu at position 54 of SEQ ID NO:2 with Pro, a substitution of Thr at position 72 of SEQ ID NO:2 with Ser, a substitution of His at position 91 of SEQ ID NO:2 with Tyr, a substitution of Thr at position 93 of SEQ ID NO:2 with Gln, a substitution of Thr at position 93 of SEQ ID NO:2 with Asn, a substitution of Pro at position 96 of SEQ ID NO:2 with Ala, a substitution of Pro at position 96 of SEQ ID NO:2 with Val, and a substitution of Thr at position 97 of SEQ ID NO:2 with Ser, and wherein the positions are numbered according to the Kabat numbering system.

According to an embodiment, the light chain variable domain comprises the following amino acid substitutions:

(i) a substitution of Thr at position 93 of SEQ ID NO:2 with Gln, a substitution of Pro at position 96 of SEQ ID NO:2 with Ala, and a substitution of Thr at position 97 of SEQ ID NO:2 with Ser (SEQ ID NO:5); or (ii) a substitution of Ser at position 50 of SEQ ID NO:2 with Thr, a substitution of Ala at position 51 of SEQ ID NO:2 with Thr, a substitution of Ser at position 52 of SEQ ID NO:2 with Thr, a substitution of Phe at position 53 of SEQ ID NO:2 with Trp, a substitution of Leu at position 54 of SEQ ID NO:2 with Pro, a substitution of Thr at position 72 of SEQ ID NO:2 with Ser, a substitution of His at position 91 of SEQ ID NO:2 with Tyr, a substitution of Thr at position 93 of SEQ ID NO:2 with Asn, and a substitution of Pro at position 96 of SEQ ID NO:2 with Val (SEQ ID NO:7).

The position 50 according to the Kabat numbering system means a 50th amino acid of SEQ ID NO:2 (Ser), the position 51 according to the Kabat numbering system means a 51th amino acid of SEQ ID NO:2 (Ala), the position 52 according to the Kabat numbering system means a 52th amino acid of SEQ ID NO:2 (Ser), the position 53 according to the Kabat numbering system means a 53th amino acid of SEQ ID NO:2 (Phe), the position 54 according to the Kabat numbering system means a 54th amino acid of SEQ ID NO:2 (Leu), the position 72 according to the Kabat numbering system means a 72th amino acid of SEQ ID NO:2 (Thr), the position 91 according to the Kabat numbering system means a 91th amino acid of SEQ ID NO:2 (His), the position 93 according to the Kabat numbering system means a 93th amino acid of SEQ ID NO:2 (Thr), the position 96 according to the Kabat numbering system means a 96th amino acid of SEQ ID NO:2 (Pro), and the position 97 according to the Kabat numbering system means a 97th amino acid of SEQ ID NO:2 (Thr).

According to an embodiment, the present antibody variant or antigen-binding fragment thereof comprises (a) a heavy chain variable domain selected from the group consisting of SEQ ID NO:3, SEQ ID NO:4 and SEQ ID NO:6; and (b) a light chain variable domain selected from the group consisting of SEQ ID NO:2, SEQ ID NO:5 and SEQ ID NO:7.

According to an embodiment, the present antibody variant or antigen-binding fragment thereof comprises the following light and heavy chain variable domains:

(i) a light chain variable domain of SEQ ID NO:2 and a heavy chain variable domain of SEQ ID NO:3;

(ii) a light chain variable domain of SEQ ID NO:2 and a heavy chain variable domain of SEQ ID NO:4;

(iii) a light chain variable domain of SEQ ID NO:5 and a heavy chain variable domain of SEQ ID NO:3; or (iv) a light chain variable domain of SEQ ID NO:7 and a heavy chain variable domain of SEQ ID NO:6.

The antibody of the present invention includes, but not limited to, monoclonal antibody, polyclonal antibody, human antibody, humanized antibody, chimeric antibody, single-chain Fvs (scFV), single-chain antibody, Fab fragment, F(ab') fragment, disulfide-linked Fvs (sdFV) and anti-idiotype (anti-Id) antibody, and epitope-binding fragment thereof.

According to an embodiment, the antibody variants of the present invention are a humanized antibody.

The present antibody or its antigen-binding fragment includes analogs of amino acid sequences set forth in the appended Sequence Listing, which are capable of specifically recognizing HER2. For example, amino acid sequence of antibody may be altered to improve binding affinity and/or the other biological characteristics of the antibody, for example including the alterations prepared by deletion, insertion and/or substitution of amino acid residues of the antibody. Such amino acid variations may be provided on the basis of a relative similarity of amino acid side chains, e.g., hydrophobicity, hydrophilicity, charge and size. By the analysis for size, shape and type of the amino acid side chains, it could be clear that all of arginine, lysine and histidine residues are those having positive charge; alanine, glycine and serine have a similar size; phenylalanine, tryptophan and tylosin have a similar shape. Accordingly, based on these considerable factors, arginine, lysine and histidine; alanine, glysine and serine; and phenylalanine, tryptophane and tylosin may be considered to be biologically functional equivalents.

For introducing mutation, a hydropathic index of amino acids may be considered. Based on the hydrophobicity and the charge, the hydropathic index is given to each amino acid: isoleucine (+4.5); valine (+4.2); leucine (+3.8); phenylalanine (+2.8); cysteine (+2.5); methionine (+1.9); alanine (+1.8); glysine (−0.4); threonine (−0.7); serine (−0.8); tryptophane (−0.9); tylosin (−1.3); proline (−1.6); histidine (−3.2); glutamate (−3.5); glutamine (−3.5); aspartate (−3.5); asparagin (−3.5); lysine (−3.9); and arginine (−4.5).

For providing an interactive biological function of proteins, the hydropathic index of the amino acid is very important. It is well known to one of skill in the art that variations can possess a similar biological activity only where proteins are replaced with amino acids having similar hydropathic index. Where variations are intended to introduce based on the hydropathic index, the substitution is preferably performed between amino acid residues having no more than ±2 difference in hydropathic index values more preferably within ±1, much more preferably within ±0.5.

It would be also obvious to those of skill in the art that substitutions of amino acids with other amino acids having similar hydrophilicity values may result in the generation of variants having biologically equivalent activities. As disclosed in U.S. Pat. No. 4,554,101, each amino acid residue is assigned the following hydrophilicity values: arginine (+3.0); lysine (+3.0); aspartate (+3.0±1); glutamate (+3.0±1); serine (+0.3); asparagin (+0.2); glutamine (+0.2); glysine (0); threonine (−0.4); proline (−0.5±1); alanine (−0.5); histidine (−0.5); cysteine (−1.0); methionine (−1.3); valine (−1.5); leucine (−1.8); isoleucine (−1.8); tylosin (−2.3); phenylalanine (−2.5); tryptophane (−3.4).

The alteration of amino acid residues not to substantially impair protein activity is well known to one skilled in the art (H. Neurath, R. L. Hill, The Proteins, Academic Press, New York, 1979). Such amino acid alteration includes Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly, but not limited to.

Considering the afore-mentioned variations having biologically equivalent activities, it could be understood that either antibody of this invention or the nucleic acid encoding the same includes substantially identical sequences to the sequences set forth in the appended Sequence Listing. The substantially identical sequences refers to those showing preferably at least 61%, more preferably at least 70%, still more preferably at least 80%, most preferably at least 90% nucleotide similarity to the sequences of the appended Sequence Listing, as measured using one of the sequence comparison algorithms. Methods of alignment of sequences for comparison are well-known in the art. Various programs and alignment algorithms are described in: Smith and Waterman, *Adv. Appl. Math.* 2:482 (1981); Needleman and Wunsch, *J. Mol. Bio.* 48:443 (1970); Pearson and Lipman, *Methods in Mol. Biol.* 24: 307-31 (1988); Higgins and Sharp, *Gene* 73:237-44 (1988); Higgins and Sharp, *CABIOS* 5: 151-3 (1989); Corpet et al., *Nuc. Acids Res.* 16:10881-90 (1988); Huang et al., *Comp. Appl. BioSci.* 8:155-65 (1992); and Pearson et al., *Meth. Mol. Biol.* 24:307-31 (1994). The NCBI Basic Local Alignment Search Tool (BLAST) (Altschul et al., *J. Mol. Biol.* 215: 403-10 (1990)) is available from several sources, including the National Center for Biological Information (NBCI, Bethesda, Md.) and on the Internet, for use in connection with the sequence analysis programs blastp, blasm, blastx, tblastn and tblastx. It can be accessed at http://www.ncbi.nlm.nih.gov/BLAST/. A description of how to determine sequence identity using this program is available at http://www.ncbi.nlm.nih.gov/BI-AST/blast help.html.

According to an embodiment, the antibody variant or its antigen-binding fragment of the present invention is an immunoconjugate. The present immunoconjugate, i.e., antibody variant-functional molecule may be used to prevent, treat or diagnose cancers overexpressing HER2 since HER2 is a molecule expressed on the surface of cancer cells. The functional molecule includes chemical substances, radionuclides, immunotherapeutic agents, cytokines, chemokines, toxins, biological agents and enzyme inhibitors.

The chemical substance is an antitumor agent such as, but not limited to, acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, *Bacillus calmette-guerin* (BCG), Baker's Antifol, beta-2'-deoxythioguanosine, bisantrene HCl, bleomycin sulfate, busulfan, buthionine sulfoximine, BWA 773U82, BW 502U83/HCl, BW 7U85 mesylate, ceracemide, carbetimer, carboplatin, carmustine, chlorambucil, chloroquinoxaline-sulfonamide, chlorozotocin, chromomycin A3, cisplatin, cladribine, corticosteroids, *Corynebacterium parvum*, CPT-11, crisnatol, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, doxorubicin, echinomycin, edatrexate, edelfosine, eflornithine, Elliott's solution, elsamitrucin, epirubicin, esorubicin, estramustine phosphate, estrogens, etanidazole, ethiofos, etoposide, fadrazole, fazarabine, fenretinide, filgrastim, finasteride, flavone acetic acid, floxuridine, fludarabine phosphate, 5-fluorouracil, Fluosor™, flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCl, ifosfamide, interferon alfa, interferon beta, interferon gamma, interleukin-1 alpha and beta, interleukin-3, interleukin-4, interleukin-6,4-ipomeanol, iproplatin, isotretinoin, leucovorin calcium, leuprolide acetate, levamisole, liposomal daunorubicin, liposome-encapsulated doxorubicin, lomustine, Ionidamine, maytansine, mechlorethamine hydrochloride, melphalan, menogaril, merbarone, 6-mercaptopurine, mesna, methanol extraction residue of *Bacillus calmette-guerin*, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor, uracil mustard, vinblastine sulfate, vincristine sulfate, vindesine, vinorelbine, vinzolidine, Yoshi 864, zorubicin, cytosine arabinoside, etoposide, melphalan, taxotere, taxol and mixtures thereof.

II. Nucleic Acid Molecules and Recombinant Vectors

In another aspect of this invention, there is provided a nucleic acid molecule encoding a heavy chain variable domain of the anti-ErbB2 antibody variant or antigen-binding fragment thereof.

In still another aspect of this invention, there is provided a nucleic acid molecule encoding a light chain variable domain of the anti-ErbB2 antibody variant or antigen-binding fragment thereof.

The term used herein "nucleic acid molecule" comprehensively refers to a DNA (gDNA and cDNA) or RNA molecule, and the basic nucleotides of nucleic acid molecule also include analogues with modified sugar or base as well as natural nucleotides (Scheit, Nucleotide Analogs, John Wiley, New York (1980); Uhlman and Peyman, Chemical Reviews, 90:543-584 (1990)). The sequence of the present nucleic acid molecule encoding the variable region of heavy and light chain could be modified. Such modification includes addition, deletion or non-conservative or conservative substitution of nucleotide.

According to an embodiment, the nucleic acid molecule encoding a heavy chain variable domain encodes a heavy chain variable domain of SEQ ID NO:3, SEQ ID NO:4 or SEQ ID NO:6, and the nucleic acid molecule encoding a light chain variable domain encodes a light chain variable domain of SEQ ID NO:2, SEQ ID NO:5 or SEQ ID NO:7.

According to an embodiment, the present nucleic acid molecule is comprised in a nucleic acid molecule encoding a whole heavy chain or a whole light chain.

The nucleic acid molecule of this invention also includes a nucleotide sequence sharing substantial homology with the above nucleotide sequence. The substantial homology means the nucleotide sequence sharing homology of at least 80%, more preferably 90% and most preferable 95% by sequence alignment analysis using maximal alignment between the nucleotide sequence of this invention and other random sequences and algorithm ordinarily known to those skilled in the art.

In still further aspect of this invention, there is provided a recombinant vector comprising (a) the present nucleic acid molecule encoding a heavy chain variable domain; and (b) the present nucleic acid molecule encoding a light chain variable domain.

The term used herein "vector" is a tool for expressing a target gene in a host cell, including a plasmid vector; a cosmid vector; and a virus vector such as a bacteriophage vector, an adenovirus vector, a retrovirus vector and an adeno-associated virus vector, and preferably a plasmid vector.

According to an embodiment, the nucleic acid molecules encoding the variable region of light and heavy chain are operatively linked to a promoter.

The term used herein "operatively linked" refers to functional linkage between a nucleic acid expression control sequence (e.g., a promoter, signal sequence, or array of transcription factor binding sites) and a second nucleic acid sequence, wherein the expression control sequence affects transcription and/or translation of the nucleic acid corresponding to the second sequence.

According to an embodiment, the recombinant vector comprises (a) a nucleic acid molecule encoding a heavy chain variable domain of SEQ ID NO:3, SEQ ID NO:4 or SEQ ID NO:6; and (b) a nucleic acid molecule encoding a light chain variable domain of SEQ ID NO:2, SEQ ID NO:5 or SEQ ID NO:7.

According to an embodiment, the recombinant vector comprises the following nucleic acid molecule:
 (i) a nucleic acid molecule encoding a heavy chain variable domain of SEQ ID NO:3, and a nucleic acid molecule encoding a light chain variable domain of SEQ ID NO:2;
 (ii) a nucleic acid molecule encoding a heavy chain variable domain of SEQ ID NO:4, and a nucleic acid molecule encoding a light chain variable domain of SEQ ID NO:2;
 (iii) a nucleic acid molecule encoding a heavy chain variable domain of SEQ ID NO:3, and a nucleic acid molecule encoding a light chain variable domain of SEQ ID NO:5; or
 (iv) a nucleic acid molecule encoding a heavy chain variable domain of SEQ ID NO:6, and a nucleic acid molecule encoding a light chain variable domain of SEQ ID NO:7.

The vector system of this invention may be performed by various methods known to those skilled in the art and its practical method is described in Sambrook et al., *Molecular Cloning, A Laboratory Manual*, Cold Spring Harbor Laboratory Press (2001), which is herein incorporated by reference.

Typically, the vector of this invention may be constructed as cloning or expression vector. In addition, the vector of this invention may be constructed using a prokaryotic or eukaryotic cell as a host cell. For instance, it is common to include a strong promoter for transcription (e.g., tac promoter, lac promoter, lacUV5 promoter, lpp promoter, $p_L^\lambda$ promoter, $p_R^\lambda$ promoter, rac5 promoter, amp promoter, recA promoter, SP6 promoter, trp promoter and 17 promoter, and so on), a ribosomal binding site for translation initiation, and a transcription/translation termination sequence where each a vector of this invention and a prokaryotic cell is used in an expression vector and the host cell, *E. coli* (e.g., HB1O1, BL21, DH5α, etc.) as a host cell may utilize a promoter and operator region for tryptophan biosynthesis pathway (Yanofsky, C, *J. Bacterial.*, 158:1018-1024 (1984)), and $p_L^\lambda$ promoter (Herskowitz, I. and Hagen, D., *Ann. Rev. Genet*, 14:399-445 (1980)) as a regulatory region. *Bacillus* as the host cell may use the promoter of a toxic protein gene of *Bacillus thuringiensis* (*Appl. Environ. Microbiol.* 64:3932-3938 (1998); *Mol. Gen. Genet.* 250:734-741 (1996)), or any promoter enabling to be expressed in *Bacillus* as the regulatory region.

The suitable vector used in this invention might be constructed by manipulating a plasmid (example: pCL, pSC101, pGV1106, pACYC177, CoIE1, pKT230, pME290, pBR322, pUC8/9, pUC6, pBD9, pHC79, pIJ61, pLAFR1, pHV14, pGEX series, pET series and pUC19), a phage (example: λgt4•λB, λ-Charon, λΔzl and M13) or a virus (example: SV40) commonly used by one ordinarily skilled in the art.

According to an embodiment, the recombinant vector is constructed using pCL or pCLS05 expression vector (Korea Patent Application No. 10-2011-0056685).

On the other hand, where the present vector is an expression vector, and its host cell is an eukaryotic cell, the promoter derived from genome of animal cell (example: methallothionein promoter, β-actin promoter, human hemoglobin promoter and human muscle creatine promoter) or mammalian virus (example: adenovirus late promoter, vaccinia virus 7.5K promoter, SV40 promoter, cytomegalovirus promoter, tk promoter of HSV, mouse mammary tumor virus (MMTV) promoter, LTR promoter of HIV, promoter of moloney virus, Epstein barr virus (EBV) and Rous sarcoma virus (RSV)) might be used, and polyadenylated sequence might be commonly used as the transcription termination sequence. In an embodiment, the vector of this invention includes CMV promoter.

The vector of this invention could be fused with other sequences to purify an antibody expressed from it. For example, a fused sequence includes glutathione-S-transferase (Pharmacia, USA), maltose-binding protein (NEB, USA), FLAG (IBI, USA) and 6× His (hexahistidine; Quiagen, USA) and so on. Since the protein expressed in the vector of the present invention is antibody, expressed antibody could be also purified throughout protein A column in an easy manner without additive sequences for purification.

On the other hand, the expression vector of this invention includes an antibiotics-resistance gene known to those ordinarily skilled in the art as a selection marker, for example resistant genes against ampicillin, gentamycin, carbenicillin, chloramphenicol, streptomycin, kanamycin, geneticin, neomycin and tetracycline.

In the vector expressing the antibody or its part of the present invention, it is possible to utilize one vector system co-expressing the light and heavy chain in single vector or the other vector system expressing each light and heavy chain in independent vector. In latter system, both vectors are introduced into the host cell by co-transformation or targeted transformation. Co-transformation is a method in which each vector DNA encoding a light and heavy chain gene is simultaneously introduced into the host cells and then the vectors expressing both light and heavy chains are selected. In targeted transformation, cells transformed with a vector containing a light chain (or heavy chain) gene are selected, and the selected cells expressing the light chain (or heavy chain) are again transformed with a vector containing a heavy chain (or light chain) gene to finally select cells expressing both light and heavy chains. As described in the examples below, the antibody was prepared by the vector system co-expressing the light and heavy chains in a single vector.

III. Transformants

In still another aspect of this invention, there is provided a host cell transformed with the above-described recombinant vector.

The host cells in which the present vector is stably and successively cloned and expressed, also utilize any one known to those skilled in the art, for example prokaryotic host cells including *Escherichia coli*, *Bacillus* sp. strains such as *Bacillus subtilis* and *Bacillus thuringiensis*, *Streptomyces*, *Pseudomonas* (e.g., *Pseudomonas putida*, *Proteus mirabilis*) or *Staphylococcus* (e.g., *Staphylococcus carnosus*), but not limited to.

The suitable eukaryotic host cell of the above vector includes fungi (e.g., *Aspergillus* species), yeasts (e.g., *Pichia pastoris*, *Saccharomyces cerevisiae*, *Schizosaccharomyces* and *Neurospora crassa*), other lower eukaryotic cells and cell derived from higher eukaryotic cells such as insect cells. In addition, mammalian-derived cells might be used as the host cells. Preferably, the host cells include, but not limited to, COS7 cell (monkey kidney cell), NSO cell, SP2/0, CHO (Chinese hamster ovary) cell, W138, BHK (baby hamster kidney) cell, MDCK, myeloma cell line, HuT 78 cell and 293 cell. More preferably, the host cell is CHO cell.

The method using microorganisms such as *E. coli* has higher productivity than that using animal cell, but it is not suitable to produce an intact Ig antibody due to glycosylation. However, the method could be used in the production of Fab and Fv.

In this specification, "transformation" and/or "transfection" introduced into the host cells also includes any one of methods by which the nucleic acid is introduced into organisms, cells, tissues or organs and may be performed by selecting a suitable standard technique according to the host cells, as known to those skilled in the art. These standard techniques include, but not limited to, electroporation, protoplast fusion, $CaPO_4$ precipitation, $CaCl_2$ precipitation, agitation with silicon carbide fiber, Agrobacteira-mediated transformation, and PEG-, dextran sulfate-, lipopectamine- and dry/inhibition-mediated transformation.

IV. Method of Preparing the Anti-ErbB2 Antibody Variant or Antigen-Binding Fragment Thereof In still further aspect of this invention, there is provided a method of preparing the anti-ErbB2 antibody variant or antigen-binding fragment thereof, comprising: (a) culturing a host cell transformed with the present recombinant vector; and (b) expressing an anti-ErbB2 antibody variant or antigen-binding fragment thereof in the host cell.

The culture of transformed host cells in the antibody preparation may be carried out according to suitable media and culture conditions well-known in the art. The culture process may be feasible manipulated according to selected strains known to those skilled in the art. Various culture processes are disclosed in various references (for example, James M. Lee, *Biochemical Engineering*, Prentice-Hall International Editions, 138-176). Cell culture is divided into suspension and adhesion culture method according to cell growth pattern and into batch, fermentation and continuous culture according to culture method. The medium used in the culture has to satisfy required conditions of particular strain.

The medium for animal cell culture includes various carbon sources, nitrogen sources and trace elements. The example of carbon sources to be used includes a carbohydrate such as glucose, sucrose, lactose, fructose, maltose, starch and cellulose, a lipid such as soybean, sunflower, castor and coconut oil, a fatty acid such as palmitic acid, stearic acid and linoleic acid, an alcohol such as glycerol and ethanol, and an organic acid such as acetate. These carbon sources may be used either alone or in combination with each other. The example of nitrogen sources to be used includes an organic nitrogen source such as peptone, yeast extract, malt extract, corn steep liquid (CSL) and soybean-wheat, and an inorganic nitrogen source such as urea, ammonium sulfate, ammonium chloride, ammonium phosphate, ammonium carbonate and ammonium nitrate. These nitrogen sources may be used either alone or in combination with each other. The medium may include not only $KH_2PO_4$, $K_2HPO_4$ and sodium-containing salts thereof as a phosphate source but also metal salt such as magnesium sulfate and iron sulfate. In addition, the medium may include amino acids, Vitamins and suitable precursors.

During culture, pH of culture solution may be adjusted by adding chemical compounds such as ammonium hydrate, potassium hydrate, ammonia, phosphate and sulfate in a predetermined manner. Bubble production may be also inhibited using an antifoaming agent such as polyglycol ester during culture. Meanwhile, oxygen or oxygen-containing gas (e.g., air) is introduced into culture to maintain aerobic state of culture. The temperature of culture is maintained at a range of from 20° C. to 45° C., and preferably from 25° C. to 40° C.

Antibodies obtained by culturing of transformed host cells may be used in unpurified condition and may be used through purification with high-purity according to further various conventional methods, for example dialysis, salt precipitation and chromatography. Among them, chromatography is used as the most useful method and kinds and orders of column may be selected from ion-exchange chromatography, size-exclusion chromatography and affinity chromatography according to characteristics of antibody, culture methods, and so on.

V. Pharmaceutical Compositions or Methods for Preventing or Treating a Cancer

In still further aspect of this invention, there is provided a pharmaceutical composition for preventing or treating a cancer, comprising: (a) a therapeutically effective amount of the anti-ErbB2 antibody variant or antigen-binding fragment thereof; and (b) a pharmaceutically acceptable carrier.

In still further aspect of this invention, there is provided a method of preventing or treating a cancer, comprising administering to a subject in need thereof a therapeutically effective amount of the pharmaceutical composition.

The term used herein "prevention" is used in the broadest sense to include, complete or partial blocking and slowing down of the progression of the disease as well as the delay of the unset of the more serious form of the disease, and the term "treatment" includes partial or total inhibition of cancer growth, as well as partial or total destruction of the cancer cells.

According to an embodiment, the cancer is cancers overexpressing HER2. In a specific embodiment, the cancer is selected from the group consisting of breast cancer, ovarian cancer, gastric cancer, lung cancer, renal cell carcinoma, rectal cancer, pancreatic cancer, bladder cancer, prostate cancer, head and neck cancer, endometrial cancer, salivary gland tumor, colon cancer, and thyroid cancer. In another embodiment, the cancer is breast cancer or gastric cancer. As used herein, the term "cancer overexpressing HER2" refers to a cancer having a significantly higher level of cell surface-expressed HER2 as compared with non-cancer cells. This overexpression may be induced by gene amplification, or an increase in transcription or translation.

The pharmaceutically acceptable carrier may be conventional one for formulation, including lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methyl hydroxy benzoate, propylhydroxy benzoate, talc, magnesium stearate, and mineral oils, but not limited to. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

The pharmaceutical composition according to the present invention may be administered via the oral or parenterally. When the pharmaceutical composition of the present invention is administered parenterally, it can be done by intravenous, subcutaneous, intramuscular, intraperitoneal, endothelial, local, spleen, lung or rectal administration. For oral administration, active ingredients of oral compositions can be coated or formulated to be protected from hydrolysis in stomach. In addition, the pharmaceutical compositions can be administered by random device in which active ingredients are moved into targeted cells.

A suitable dose of the pharmaceutical composition of the present invention may vary depending on pharmaceutical formulation methods, administration methods, the patient's age, body weight, sex, severity of diseases, diet, administration time, administration route, an excretion rate and sensitivity for a used pharmaceutical composition. Preferably, the pharmaceutical composition of the present invention is administered with a daily dose of 0.001-100 mg/kg (body weight). The term "pharmaceutically effective amount" refers to an amount suitable to prevent or treat the cancer.

According to the conventional techniques known to those skilled in the art, the pharmaceutical composition may be formulated with pharmaceutically acceptable carrier and/or vehicle as described above, finally providing several forms including a unit dose form and a multi-dose form. Formulation may be oil or aqueous media, resuspension or emulsion, extract, powder, granule, tablet and capsule and further comprise dispersant or stabilizer.

The antibody compositions of this invention may be independently administered as a therapeutic agent or be sequentially or simultaneously administered with a conventional therapeutic agent.

The antibody variant of this invention may be administered to a subject in the form of a conjugate of antibody variant-therapeutic agent (functional molecules) to treat cancers, as described above. Various conditions appropriate and desirable for targeting drugs to specific target sites have been reported in e.g., *Plenum Press*, New York and London, (1982) 19-30.

The features and advantages of this invention will be summarized as follows:

(a) The antibody variants of the present invention are capable of binding to ErbB2 with high affinity. Especially, affinity of the present antibody variants for ErbB2 is improved by up to maximum 8-fold when compared with the conventional therapeutic antibody 4D5.

(b) The antibody variants of the present invention have superior inhibitory activity to cancer cell proliferation. Especially, inhibitory activity of the present antibody variants to gastric cancer cell proliferation is about 3.5-fold higher than 4D5

(c) Therefore, the antibody variants of the present invention are ability to effectively prevent or treat various cancers with a low amount.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Construction of Phage-Displayed scFv Library Having Various CDRs

Phage-displayed scFv libraries were constructed using a phagemid vector which was designed to display scFv and pIII in the form of fusion. The structure of the vector is schematically shown in FIG. 1. The vector comprises an antibody variable domain under the control of an IPTG-inducible $P_{lac}$ promoter, and its linker sequence is GGGGSGGGSGGSS (SEQ ID NO:8). A method of preparing an anti-ErbB2 antibody (4D5, parent antibody) and its variable domain sequences are disclosed in U.S. Pat. Nos. 5,821,337 and 6,054,297.

A unique "stop template" version of the scFv display vector was used to generate libraries. We used a template phagemid vector designated as pCMTG (IG Therapy Co., Korea) with TGA stop codon inserted at position 48 (residue position according to Kabat) of the light chain. No stop codon was introduced in the heavy chain CDR3. Mutagenic oligonucleotides with degenerate NNK codons at the positions to be diversified were used to simultaneously introduce CDR diversity and remove the stop codon, whereby an open reading frame that encoded a scFv library member fused to a homodimerizing c-myc and pIII was generated.

Heavy chain and light chain CDR3 regions were first modified. To modify the Heavy chain CDR3 region, PCR was conducted using a primer set of HF (SEQ ID NO:19) and LN01_R (SEQ ID NO:9), and a primer set of HF (SEQ ID NO:19) and LN01_R (SEQ ID NO:10). PCR amplification was performed using a Bio-Rad C1000 thermal cycler according to manufacturer's instructions (Ex taq, Takara, Japan). PCR condition was as follows: denature, 95° C. for 20 sec; anneal, 57° C. for 30 sec; extend, 72° C. for 45 sec; 27 cycles. To modify the light chain CDR3 region, PCR was conducted using a primer set of LN03_F (SEQ ID NO:11) and LR (SEQ ID NO:17), and a prier set of LN04_F (SEQ ID NO:12) and LR (SEQ ID NO:17). PCR conditions were same as described above.

To construct a library in which mutations were randomly introduced in light chain CDR2, PCR was twice conducted using antibodies selected from heavy and light chain CDR3 variants as a template and NNK codons. PCR condition was as follows: denature, 95° C. for 20 sec; anneal, 57° C. for 30 sec; extend, 72° C. for 45 sec, 27 cycles. Fragment A was prepared using LF (SEQ ID NO:18) as a forward primer and a primer mixture (ratio 1:1) of LN05_R (SEQ ID NO:13) and LN06_R (SEQ ID NO:14) as a reverse primer, and fragment B was prepared using a primer set of LN0506_F (SEQ ID NO:15) and HR (SEQ ID NO:20). Then, PCR was performed using the fragments A and B as a template, and a primer set of LF (SEQ ID NO:18) and HR (SEQ ID NO:20). In addition, an additional library was prepared using antibodies selected from the group consisting of a heavy chain CDR3 variant and two light chain (CDRL2, CDRL3) variants as a template, and LF (SEQ ID NO:18) and LN07_R (SEQ ID NO:16) as a primer.

In order to construct antibody library in which randomized mutations targeting all of the CDRs and framework regions were introduced, error-prone PCR was twice carried out using heavy chain CDR3, light chain CDR3 and light chain CDR2 variants selected from the library as a template, in the following manner: the first PCR which amplification condition was 32 cycles of denaturing for 20 sec at 95° C., annealing for 30 sec 57° C., and extension for 45 sec 72° C., was conducted using GeneMorpII Random mutagenesis kit (Stratagene, USA), thereby amplifying fragments containing a light chain or a heavy chain by a primer set of LF (SEQ ID NO:18) and LR (SEQ ID NO:17), and HF (SEQ ID NO:19) and HR (SEQ ID NO:20), respectively. Then, through the second PCR using Ex taq (Takara, Japan), the resulting two PCR fragments containing a light chain or a heavy chain were amplified using a primer set of LF (SEQ ID NO:18) and HR (SEQ ID NO:20), thereby preparing scFv library. The amplification condition of second PCR was 20 cycles of denaturing for 20 sec at 95° C., annealing for 30 sec 58° C., and extension for 45 sec 72° C. Each primer sequence used for the PCR is shown in Table 1.

TABLE 1

| Primers | sequences | SEQ ID NOs. |
|---|---|---|
| LN01_R | ACTAGTGCTACTCACGGTCACCAGAGTTCCCTGTCCCCAGTAATCCAT GGCGTAMNNGCCMNNMNNMNNMNNMNNTCTAGAGCAGTAGTAC | SEQ ID NO: 9 |
| LN02_R | ACTAGTGCTACTCACGGTCACCAGAGTTCCCTGTCCCCAMNNMNNMNN MNNGTAGAAGCCATCACC | SEQ ID NO: 10 |
| LN03_F | GACTTCGCTACGTACTACTGCNNKNNKNNKNNKACCACTCCTCCGAC | SEQ ID NO: 11 |
| LN04_F | GACTTCGCTACGTACTACTGCCAACAGCACTACNNKACTNNKNNKNNK TTCGGACAAGGCAC | SEQ ID NO: 12 |
| LN05_R | TGAATCTAGATGGCACACCMNNMNNMNNGAAMNNMNNMNNGTAGATCA GCAGCTTC | SEQ ID NO: 13 |
| LN06_R | TGAATCTAGATGGCACACCMNNMNNMNNCCAMNNMNNMNNGTAGATCA GCAGCTTC | SEQ ID NO: 14 |
| LN0506_F | GGTGTGCCATCTAGATTCAGTG | SEQ ID NO: 15 |
| LN07_R | ACTAGTGCTACTCACGGTCACCAGAGTTCCCTGTCCCCAGTAATCCAT MNNGTAMNNGCCMNNMNNMNNMNNTCTAGAGCAGTAGTAC | SEQ ID NO: 16 |
| LR | GCGCGCTACTCACGGTC | SEQ ID NO: 17 |
| LF | GGCCCAGGCGGCCGATATCCAGATGAC | SEQ ID NO: 18 |
| HF | GAGCTCATGGATATCCAGATGACCCAGAG | SEQ ID NO: 19 |
| HR | GCGCGCTACTCACGGTC | SEQ ID NO: 20 |

The parent antibody comprises amino acid sequences of variable domains of the humanized antibody 4D5 (Table 2).

TABLE 2

| | amino acid sequences | SEQ ID NOs. |
|---|---|---|
| $V_H$ | EVQLVESGGGLVQPGGSLRLSCAASGFNIKDTYIHWVRQAPGKGLEWVAR IYPTNGYTRYADSVKGRFTISADTSKNTAYLQMNSLRAEDTAVYYCSRWG GDGFYAMDYWGQGTLVTVSS | SEQ ID NO: 1 |
| $V_L$ | DIQMTQSPSSLSASVGDRVTITCRASQDVNTAVAWYQQKPGKAPKLLIYSA SFLYSGVPSRFSGSRSGTDFTLTISSLQPEDFATYYCQQHYTTPPTFGQGT KVEIK | SEQ ID NO: 2 |

Prepared libraries LN01 and LN02 have randomized residues at a CDRH3 region, and prepared libraries LN03 and LN04 have randomized residues at a CDRL3 region. In addition, prepared libraries LN05, LN06 and LN07 have randomized residues at CDRL2, CDRL3 and CDRH3 regions. The randomized residues are described in Table 3. CDR positions are numbered according to Kabat system. A library prepared by the error-prone PCR, which have variants in framework regions as well as CDRs, was designated as LN08.

TABLE 3

| Librar- | Randomized positions | | |
|---|---|---|---|
| ies | CDRL2 | CDRL3 | CDRH3 |
| LN01 | — | — | 95, 96, 97, 98, 100 |
| LN02 | — | — | 100b, 100c, 101, 102 |
| LN03 | — | 89, 90, 91, 92 | — |
| LN04 | — | 93, 95, 96, 97 | — |
| LN05 | 50, 51, 52, 54, 55, 56 | 93, 95, 96, 97 | 95, 96, 97, 98, 100 |
| LN06 | 50, 51, 52, 54, 55, 56 | 93, 95, 96, 97 | 100b, 100c, 101, 102 |
| LN07 | 50, 51, 52, 54 | 93, 96, 97 | 96, 97, 98, 100b, 100c, 101, 102 |

The libraries were introduced into *E. coli* XL1-blue-MRF' (200158, Stratagene, USA) by electroporation (Sidhu et al. Methods Enzymol. 328:333-363 (2000)), and the transformants were cultured overnight under the presence of Ex12 helper phages (IG therapy, Korea) to encapsulate phagemid DNA, thereby generating phage particles displaying scFv fragments on its surface. Each library contained greater than $5 \times 10^8$ members.

Example 2

Selection of ErbB2-Specific Antibodies from scFv Libraries

ErbB2-specific antibodies were selected from the antibody libraries of Example 1. NUNC 96-well Maxisorp immunoplates were coated overnight with 2 μg/ml of capture target at 4° C., and blocked with SuperBlock™ Tris buffered saline (Pierce) for 2 hours. Phages were cultured overnight and enriched, followed by resuspension of the enriched phage in SuperBlock™ TBS and 0.05% Tween 20 (Sigma). The phage solutions were added to the coated plates at a concentration of $10^{12}$ phage particles/ml, and incubated for 2 hours. The plates were washed 10 times with PBS and 0.05% Tween 20. Then, bound phages were eluted with 0.1M glycine (pH 2.2) for 10 minutes, and subsequently the eluted solution was neutralized with 1M Tris/Cl (pH 9.0). The eluant was propagated in *E. coli* XL1-blue-MRF'.

It was difficult to select an antibody having improved affinity since the parent antibody had already high affinity ($K_D$ value of picomole). Therefore, we used three manners to select an antibody having higher affinity than the parent antibody. In the first manner, washing was carried out for maximum 44 hours to select an antibody exhibiting enhanced off-rate (Chen et al. *J Mol Biol.* 293:865-81 (1999)). In the second manner, pre-elution was performed with 0.1M glycine (pH 2.2) before final elution (Bruin et al. *Nat Biotechnol.* 17(4):397-9 (1999)). In the third manner, weakly bound antibodies were removed by treating ammonium thiocyanate before elution (Macdonald et al. *J Immunol Methods* 106: 191-4 (1988); Wang et al. *J Immunol Methods.* 241(1-2):171-84 (2000); Hur et al. *Immunol Lett.* 134(1):55-61 (2010)).

Figure 2:
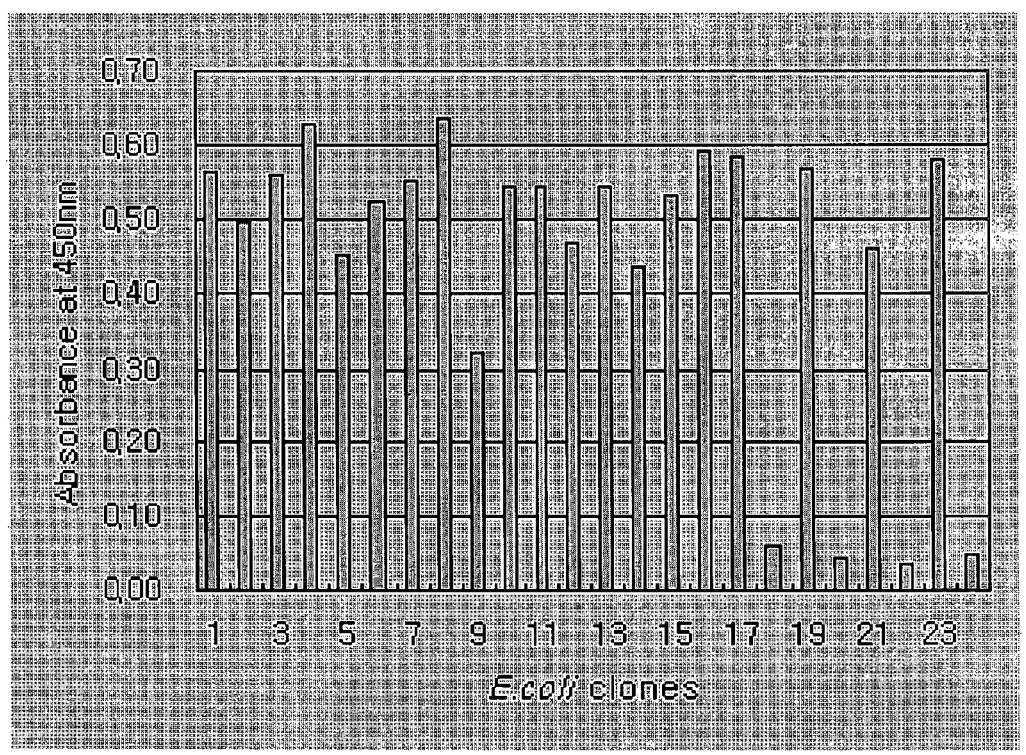
FIG. 2 represents results of monoclonal ELISA for selecting E. coli clones producing scFv-pIII binding to ErbB2.

After the selection, individual clones were grown in a 96-well format in 500 μl of 2YT broth supplemented with carbenicillin and ampicillin, and the culture supernatants were used in phage ELISA to detect phage-displayed scFv that bound to antigen-coated plates but not to BSA-coated plates (FIG. 2). A clone which exhibits OD value more than 0.5 on the antigen-coated plates as compared with BSA-coated plates and maintains binding force in the presence of 1.0M ammonium thiocyanate, was determined as a ErbB2-specific variant. After repetitive experimentation for 4-5 times, the ErbB2-specific variants were selected by screening the individual clones from the libraries.

The ErbB2-specific variants were subjected to DNA sequence analysis. As a result, it was identified that one ErbB2-specific variant (AH06) had amino acid substitutions at positions 98, 100c, 101 and 102 (residue position according to Kabat) of the heavy chain variable domain of the parent antibody 4D5, and that the other variants had additional amino acid substitutions at Kabat positions 41, 96, 97 or 100b of the heavy chain variable domain, or/and at Kabat positions 50, 51, 52, 53, 54, 72, 91, 93, 96 or 97 of the light chain variable domain as well as the amino acid substitutions as described above.

Each substituted residue was combined to select optimum ErbB2-specific variants. Selected ErbB2-specific variants were named as AH06, AH16, A058 or A091. The heavy chain of the humanized antibody AH06 was a variant of the 4D5 antibody heavy chain, and comprised amino acid sequences of SEQ ID NOs: 2 and 3. The humanized antibody AH16 comprised amino acid sequences of SEQ ID NOs: 2 and 4. The humanized antibody A058 comprised amino acid sequences of SEQ ID NOs: 3 and 5. The humanized antibody A091 comprised amino acid sequences of SEQ ID NOs: 6 and 7. Their amino acid sequences of heavy and light chain variable domains are described in Table 4. Further, FIGS. 3 and 4 disclose compare results of the amino acid sequences between 4D5 antibody and the selected antibodies.

TABLE 4

| | amino acid sequences | SEQ ID NOs. |
|---|---|---|
| $V_H$ | EVQLVESGGGLVQPGGSLRLSCAASGFNIKDTYIHWVRQAPGKGLEWVARI YPTNGYTRYADSVKGRFTISADTSKNTAYLQMNSLRAEDTAVYYCSRWGGW GFYAFALWGQGTLVTVSS | SEQ ID NO: 3 |
| $V_H$ | EVQLVESGGGLVQPGGSLRLSCAASGFNIKDTYIHWVRQAPGKGLEWVARI YPTNGYTRYADSVKGRFTISADTSKNTAYLQMNSLRAEDTAVYYCSRWNAK GFYSFVHWGQGTLVTVSS | SEQ ID NO: 4 |
| $V_L$ | DIQMTQSPSSLSASVGDRVTITCRASQDVNTAVAWYQQKPGKAPKLLIYSA SFLYSGVPSRFSGSRSGTDFTLTISSLQPEDFATYYCQQHYQTPASFGQGT KVEIK | SEQ ID NO: 5 |
| $V_H$ | EVQLVESGGGLVQPGGSLRLSCAASGFNIKDTYIHWVRQARGKGLEWVARI YPTNGYTRYADSVKGRFTISADTSKNTAYLQMNSLRAEDTAVYYCSRWGGW GFYAFALWGQGTLVTVSS | SEQ ID NO: 6 |

TABLE 4-continued

| amino acid sequences | SEQ ID NOs. |
|---|---|
| $V_L$ DIQMTQSPSSLSASVGDRVTITCRASQDVNTAVAWYQQKPGKAPKLLIYTT TWPYSGVPSRFSGSRSGTDFSLTISSLQPEDFATYYCQQYYNTPVTFGQGT KVEIK | SEQ ID NO: 7 |

Example 3

Construction of Vectors Expressing Anti-ErbB2 Antibody Heavy and Light Chains

An expression vector (pCLS05 disclosed in Korea Patent application No. 2011-0056685) was used to replace variable domain genes of the humanized antibodies (scFv) prepared in Example 1 with whole genes of a humanized antibody. First of all, to insert the $V_H$ gene of the antibodies into the expression vector, the $V_H$ gene was cleaved with restriction enzymes EcoRI|XhoI (NEB, USA) for 2 hours at 37° C., followed by identification of 1.4 kb gene fragments by 1.5% agarose gel electrophoresis and ethidium bromide staining. Similarly, the expression vector pCLS05 was also cleaved with restriction enzymes EcoRI|XhoI, and cleaved expression vector of about 7.5 kb was identified. Then, each gene fragment was retrieved using QIA gel extraction kit (Qiagen, USA), and then reacted overnight at 16° C. using T4 DNA ligase (Takara Holdings, Japan), followed by transformation of E. coli DH5α. The resulting transformants were cultured overnight in LB medium containing 100 μg/ml of ampicillin, followed by harvest of plasmids. It was identified by sequence analysis that the whole gene of the heavy chain was inserted into the vector.

To insert a whole gene of the light chain into the expression vector pCLS05 having the whole gene of the humanized antibody heavy chain, a whole gene of the light chain was cleaved with restriction enzymes HindIII/BamHI (NEB, USA) for 2 hours at 37° C., followed by identification of a gene fragment of 0.7 kb size by 1.5% agarose gel electrophoresis and ethidium bromide staining. Similarly, the expression vector pCLS05 was also cleaved with restriction enzymes EcoRI|XhoI, and cleaved expression vector of about 8.8 kb size was identified. Then, each gene fragment was retrieved using QIA gel extraction kit (Qiagen, USA), and then reacted overnight at 16° C. using T4 DNA ligase (Takara Holdings, Japan), followed by transformation of E. coli DH5α. The resulting transformants were cultured overnight in LB medium containing 100 μg/ml of ampicillin, followed by harvest of plasmids. It was identified by sequence analysis that the whole gene of the light chain was inserted into the vector.

Example 4

Transformation for Expressing Humanized Antibodies

To measure activity of the humanized antibody, FreeStyle™ CHO-s cells (#R800-07, Invitrogen) were transformed with the expression vector as prepared in Example 3. A FreeStyle™ CHO expression medium (Invitrogen, USA) supplemented with 8 mM L-glutamine (25030-081, Gibco) was used to culture CHO cells. The cell was incubated for 2-3 days at 37° C. in a humidified 5% $CO_2$ incubator, followed by collection of the cells by centrifugation at 1,200 rpm for 5 min at 25° C. The collected cell was then stained with 0.4% trypan blue (Fluka), and stained cells were counted by hematocytometer.

The CHO-s cell was subcultured in a new medium to obtain cells having cell density of $5 \times 10^5$ cells/ml and viability of >95%. After 132 μg of the expression vector and 130 μl of FreeStyle™ MAX Reagent (#16447-100, Invitrogen) were reacted for 10 min, the resulting reactant was mixed with the prepared cells, followed by culture for 5 days in a $CO_2$ incubator (37° C., 5% $CO_2$, 110 rpm Orbital shaker).

Example 5

Purification of Humanized Antibodies

Humanized antibodies were obtained by culturing the transformant as prepared in Example 4 and by purifying antibodies as follows. Cells ($5 \times 10^7$) were incubated in Free Style™ CHO Expression medium (100 ml) in an Erlenmeyer flask (500 ml) for 5 days at 37° C. using a humidified 5% $CO_2$ incubator. After a cell culture solution was collected and centrifuged, the resultant was filtered to obtain a culture solution containing only antibodies. A disposable chromatography column (732-1010, BIO-RAD) packed with 1 ml Mabselect resin having the binding capacity of 30 mg human IgG/ml (17-5199-01, GE Healthcare) was used to solely purify antibodies from the culture solution. The cell culture solution in which antibodies were expressed, was passed through the Mabselect column to bind the antibodies with protein A, and passed 0.1M sodium citrate buffer to elute antibodies bound to protein A. The antibody-eluted solution was neutralized by adding Tris-Cl buffer (pH 9.0) in 1/10 volume of the eluted solution.

Buffer change was performed with PBS (pH 7.4). Prepared antibody sample was applied to PBS-wetted VIVASPIN (MWCO 30000, Sartorius, Cat. No. VS2021), followed by centrifugation at 3,000 rpm for 30 minutes at 4° C. Buffer change more than 1,000 times was done by the centrifugation for 3 times.

Figure 5:
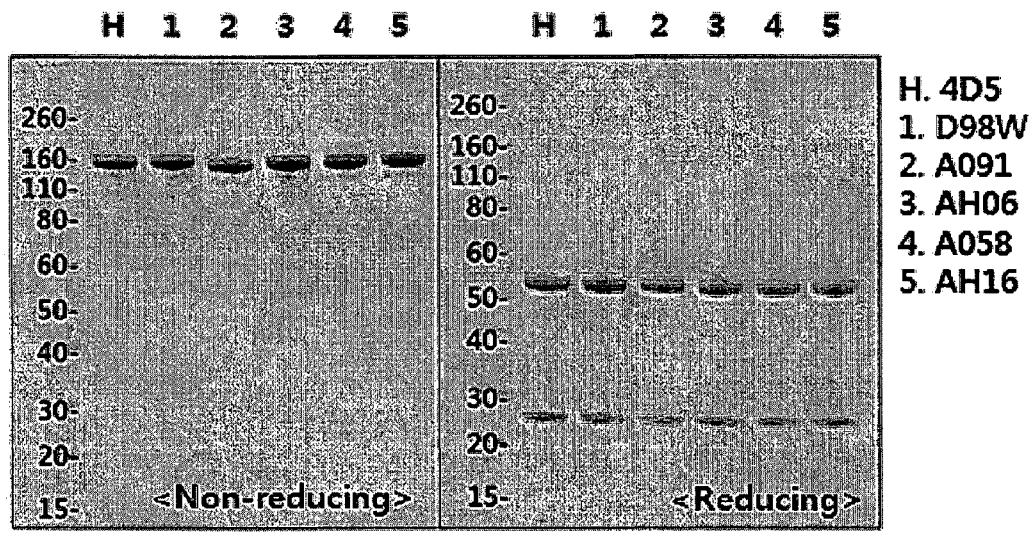
FIG. 5 represents SDS-PAGE results of the anti-ErbB2 antibody variants of the present invention, as prepared and purified from an animal cell.

The purified antibody was determined using NuPAGE Novex Bis-Tris Mini Gels 4-12% gradient (Invitrogen, Cat. No. NP0321). As a result, as shown in FIG. 5, a heavy chain protein band (50,000 Da molecular weight) and a light chain protein band (25,000 Da molecular weight) were determined (FIG. 5).

Example 6

Affinity Measurement of Anti-ErbB2 Antibodies

The binding affinity of the present anti-ErbB2 antibody variants for ErbB2 was measured. BIAcore data was obtained, as described previously (Chen et al. J Mol Biol. 293(4):865-81 (1999)). Briefly, binding affinities of the antibody variants for ErbB2 were estimated from association and dissociation rate constants measured using BIAcore™-2000 surface Plasmon resonance system (BIAcore, Inc.). Antigens were immobilized on the surface of a M5 sensor chip using an amino coupling method, as described previously (Analyt.

Biochem. 198:268-277 (1991)). ErbB2 was covalently coupled by activation of the biosensor chip using EDC (N-Ethyl-N'-(3-dimethylaminopropyl)carbodiimide) and NHS (N-Hydroxysuccinimide). ErbB2 was buffer-exchanged into 10 mM sodium-acetate, pH 4.8, and diluted to approximately 30 μg/ml. Aliquots of ErbB2 were injected at a flow rate of 5 μl/min to achieve approximately 250-300 response units (RU) of coupled proteins. A solution of 1M ethanolamine was injected as a blocking agent. For kinetic measurements, serial dilutions of 100, 50, 25, 12.5, 6.25 and 3.125 nM were injected from lower concentration to higher concentration at a flow rate of 10 μl/min for 5 min, followed by dissociation by injecting a running buffer for 30 min. Equilibrium dissociation constants, $K_D$ values from surface Plasmon resonance measurements were calculated as $k_{on}/k_{off}$. The BIAcore™ data is summarized below.

TABLE 5

| | Association constant ($k_{on}$, 1/Ms) | Dissociation constant ($k_{off}$, 1/s) | Affinity for antigen ($K_D$, M) |
|---|---|---|---|
| 4D5 | $2.09 \times 10^5$ | $8.82 \times 10^{-5}$ | $4.22 \times 10^{-10}$ |
| D98W | $3.97 \times 10^5$ | $8.89 \times 10^{-5}$ | $2.24 \times 10^{-10}$ |
| AH06 | $8.80 \times 10^5$ | $4.42 \times 10^{-5}$ | $5.02 \times 10^{-11}$ |
| AH16 | $4.04 \times 10^5$ | $1.20 \times 10^{-4}$ | $2.97 \times 10^{-10}$ |
| A058 | $5.22 \times 10^5$ | $2.78 \times 10^{-4}$ | $5.33 \times 10^{-10}$ |
| A091 | $6.44 \times 10^5$ | $6.88 \times 10^{-4}$ | $1.07 \times 10^{-9}$ |

As shown in Table 5, affinity of D98W as reported in Resi et al. 21:851-862 (2002) exhibited $K_D$ value of 224 pM, which was 2-fold increased value than that of the parent antibody 4D5 ($K_D$ value: 422 pM), while affinity of the present anti-ErbB2 antibody variant, AH06, exhibited $K_D$ value of 50.2 pM, which was 8-fold increased value than that of 4D5. Further, affinity of the present anti-ErbB2 antibody variant, AH16, exhibited $K_D$ value of 297 pM, which was approximately 2-fold increased value than that of 4D5 (Table 5).

These results clearly show that affinity of the present 4D5 variants for the antigen was remarkably improved than that of the parent antibody 4D5.

Example 7

Inhibitory Effects of Anti-ErbB2 Antibodies on Cell Proliferation

To investigate inhibitory effects of each anti-ErbB2 antibody variant on ErbB2 mediated diseases, cell proliferation-inhibitory effects of the antibody variants were assessed using gastric cancer cell line, NCI-N87 cell (ATCC accession No. CRL-5822). NCI-N87 cells were detached by trypsin-EDTA treatment, followed by suspension of detached cells in a medium to make cell concentration of $0.75 \times 10^4$ cells/ml, and the resulting cells were inoculated into a 96-well cell culture plate at 1 ml per well. After inoculation, cells were cultured for cell attachment at 37° C., 5% $CO_2$, and treated with the humanized antibodies of 10, 1, 0.1, 0.01 or 0.001 μg/ml using RPMI 1640/2% FBS medium. After reaction for approximately 6 days, WST-8 (Dojindo) was treated for color reaction, and then wavelength at 450 nm was measured.

Figure 6:
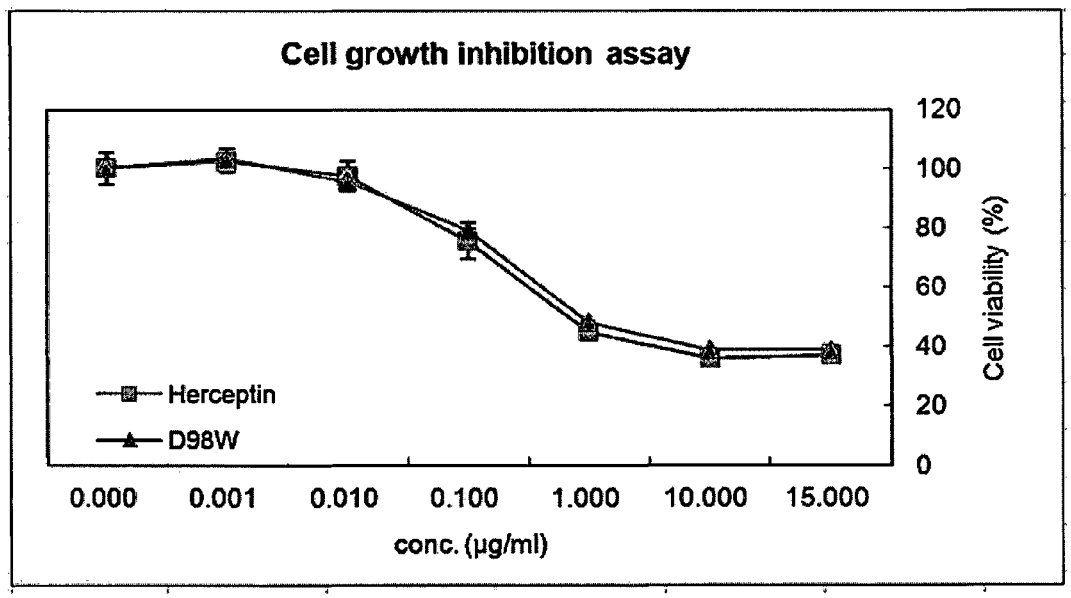

FIGS. 6-8 show cell proliferation-inhibitory effects of the present anti-ErbB2 antibody variants and 4D5 antibody on the NCI-N87 cell. As shown in FIGS. 7 and 8, cell proliferation-inhibitory effects of the present antibody variants were increased by up to about 3.5-fold when compared with 4D5 (parent antibody). In contrast, cell proliferation-inhibitory effect of D98W which has 2-fold increased affinity when compared with 4D5 as described in Example 6, was equal to that of 4D5 (FIG. 6). More specifically, efficacy of the A091 antibody ($IC_{50}$=10.3 nM) was improved nearly 2-fold than that of 4D5 ($IC_{50}$=25.4 nM), and efficacy of the A058 antibody ($IC_{50}$=4.3 nM) was improved nearly 2.5-fold than that of 4D5 ($IC_{50}$=10.4 nM) (FIG. 7). In addition, efficacy of the AH06 antibody ($IC_{50}$=3.4 nM) was improved about 3.5-fold than that of 4D5 ($IC_{50}$=11.6 nM) (FIG. 8).

The results clearly show that 4D5 variants of the present invention were improved in terms of not only affinity but also cell proliferation-inhibitory activity as compared with both the parent antibody 4D5 and the D98W antibody.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A recombinant ErbB2 antibody or antigen-binding fragment thereof, comprising the following heavy chain variable domain and light chain variable domain:
   (i) a light chain variable domain of SEQ ID NO:2 and a heavy chain variable domain of SEQ ID NO:3;
   (ii) a light chain variable domain of SEQ ID NO:2 and a heavy chain variable domain of SEQ ID NO:4;
   (iii) a light chain variable domain of SEQ ID NO:5 and a heavy chain variable domain of SEQ ID NO:3; or
   (iv) a light chain variable domain of SEQ ID NO:7 and a heavy chain variable domain of SEQ ID NO:6.

2. The antibody or antigen-binding fragment thereof according to claim 1, which is a humanized antibody.

3. The antibody or antigen-binding fragment thereof according to claim 1, comprising a light chain variable domain of SEQ ID NO:2 and a heavy chain variable domain of SEQ ID NO:3.

4. The antibody or antigen-binding fragment thereof according to claim 1, comprising a light chain variable domain of SEQ ID NO:2 and a heavy chain variable domain of SEQ ID NO:4.

5. The antibody or antigen-binding fragment thereof according to claim 1, comprising a light chain variable domain of SEQ ID NO:5 and a heavy chain variable domain of SEQ ID NO:3.

6. The antibody or antigen-binding fragment thereof according to claim 1, comprising a light chain variable domain of SEQ ID NO:7 and a heavy chain variable domain of SEQ ID NO:6.

* * * * *

SEQUENCE LISTING

```
<160> NUMBER OF SEQ ID NOS: 20

<210> SEQ ID NO 1
<211> LENGTH: 120
<212> TYPE: PRT
<213> ORGANISM: Artificial Sequence
<220> FEATURE:
<223> OTHER INFORMATION: Synthetic Construct

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
```

```
                65                  70                  75                  80
Leu Gln Met Asn Ser Leu Arg Ala Glu Asp Thr Ala Val Tyr Tyr Cys
                    85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 2
<211> LENGTH: 107
<212> TYPE: PRT
<213> ORGANISM: Artificial Sequence
<220> FEATURE:
<223> OTHER INFORMATION: Synthetic Construct

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 3
<211> LENGTH: 120
<212> TYPE: PRT
<213> ORGANISM: Artificial Sequence
<220> FEATURE:
<223> OTHER INFORMATION: Synthetic Construct

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Trp Gly Phe Tyr Ala Phe Ala Leu Trp Gly Gln
            100                 105                 110

Gly Thr Leu Val Thr Val Ser Ser
        115                 120

<210> SEQ ID NO 4
<211> LENGTH: 120
```

```
<212> TYPE: PRT
<213> ORGANISM: Artificial Sequence
<220> FEATURE:
<223> OTHER INFORMATION: Synthetic Construct

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Asn Ala Lys Gly Phe Tyr Ser Phe Val His Trp Gly Gln
            100                 105                 110

Gly Thr Leu Val Thr Val Ser Ser
        115                 120

<210> SEQ ID NO 5
<211> LENGTH: 107
<212> TYPE: PRT
<213> ORGANISM: Artificial Sequence
<220> FEATURE:
<223> OTHER INFORMATION: Synthetic Construct

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Gln Thr Pro Ala
                85                  90                  95

Ser Phe Gly Gln Gly Thr Lys Val Glu Ile Lys
            100                 105

<210> SEQ ID NO 6
<211> LENGTH: 120
<212> TYPE: PRT
<213> ORGANISM: Artificial Sequence
<220> FEATURE:
<223> OTHER INFORMATION: Synthetic Construct

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Arg Gly Lys Gly Leu Glu Trp Val
```

```
            35                  40                  45
Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Trp Gly Phe Tyr Ala Phe Ala Leu Trp Gly Gln
            100                 105                 110

Gly Thr Leu Val Thr Val Ser Ser
            115                 120

<210> SEQ ID NO 7
<211> LENGTH: 107
<212> TYPE: PRT
<213> ORGANISM: Artificial Sequence
<220> FEATURE:
<223> OTHER INFORMATION: Synthetic Construct

<400> SEQUENCE: 7

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
             20                  25                  30

Val Ala Trp Tyr Gln Gln Lys Pro Gly Lys Ala Pro Lys Leu Leu Ile
         35                  40                  45

Tyr Thr Thr Thr Trp Pro Tyr Ser Gly Val Pro Ser Arg Phe Ser Gly
 50                  55                  60

Ser Arg Ser Gly Thr Asp Phe Ser Leu Thr Ile Ser Ser Leu Gln Pro
 65                  70                  75                  80

Glu Asp Phe Ala Thr Tyr Tyr Cys Gln Gln Tyr Tyr Asn Thr Pro Val
                 85                  90                  95

Thr Phe Gly Gln Gly Thr Lys Val Glu Ile Lys
            100                 105

<210> SEQ ID NO 8
<211> LENGTH: 13
<212> TYPE: PRT
<213> ORGANISM: Artificial Sequence
<220> FEATURE:
<223> OTHER INFORMATION: Synthetic Construct

<400> SEQUENCE: 8

Gly Gly Gly Gly Ser Gly Gly Gly Ser Gly Gly Ser Ser
 1               5                  10

<210> SEQ ID NO 9
<211> LENGTH: 88
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (65)..(66)
```

<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t

<400> SEQUENCE: 9
actagtgcta ctcacggtca ccagagttcc ctgtccccag taatccatgg cgtamnngcc    60
mnnmnnmnnm nntctagagc agtagtac                                       88

<210> SEQ ID NO 10
<211> LENGTH: 66
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t

<400> SEQUENCE: 10
actagtgcta ctcacggtca ccagagttcc ctgtccccam nnmnnmnnmn ngtagaagcc    60
atcacc                                                               66

<210> SEQ ID NO 11
<211> LENGTH: 47
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t

<400> SEQUENCE: 11
gacttcgcta cgtactactg cnnknnknnk nnkaccactc ctccgac                  47

<210> SEQ ID NO 12
<211> LENGTH: 62
<212> TYPE: DNA
<213> ORGANISM: Artificial Sequence

```
<220> FEATURE:
<223> OTHER INFORMATION: Synthetic Construct
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t

<400> SEQUENCE: 12
gacttcgcta cgtactactg ccaacagcac tacnnkactn nknnknnktt cggacaaggc      60
ac                                                                    62

<210> SEQ ID NO 13
<211> LENGTH: 56
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t

<400> SEQUENCE: 13
tgaatctaga tggcacaccm nnmnnmnnga amnnmnnmnn gtagatcagc agcttc          56

<210> SEQ ID NO 14
<211> LENGTH: 56
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(28)
```

```
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t

<400> SEQUENCE: 14
tgaatctaga tggcacaccm nnmnnmnncc amnnmnnnmnn gtagatcagc agcttc          56

<210> SEQ ID NO 15
<211> LENGTH: 22
<212> TYPE: DNA
<213> ORGANISM: Artificial Sequence
<220> FEATURE:
<223> OTHER INFORMATION: Synthetic Construct

<400> SEQUENCE: 15
ggtgtgccat ctagattcag tg                                                22

<210> SEQ ID NO 16
<211> LENGTH: 88
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t

<400> SEQUENCE: 16
actagtgcta ctcacggtca ccagagttcc ctgtccccag taatccatmn ngtamnngcc       60
mnnmnnmnnm nntctagagc agtagtac                                          88

<210> SEQ ID NO 17
<211> LENGTH: 17
<212> TYPE: DNA
<213> ORGANISM: Artificial Sequence
<220> FEATURE:
<223> OTHER INFORMATION: Synthetic Construct

<400> SEQUENCE: 17
gcgcgctact cacggtc                                                      17
```

```
<210> SEQ ID NO 18
<211> LENGTH: 27
<212> TYPE: DNA
<213> ORGANISM: Artificial Sequence
<220> FEATURE:
<223> OTHER INFORMATION: Synthetic Construct

<400> SEQUENCE: 18
ggcccaggcg gccgatatcc agatgac                                    27

<210> SEQ ID NO 19
<211> LENGTH: 29
<212> TYPE: DNA
<213> ORGANISM: Artificial Sequence
<220> FEATURE:
<223> OTHER INFORMATION: Synthetic Construct

<400> SEQUENCE: 19
gagctcatgg atatccagat gacccagag                                  29

<210> SEQ ID NO 20
<211> LENGTH: 17
<212> TYPE: DNA
<213> ORGANISM: Artificial Sequence
<220> FEATURE:
<223> OTHER INFORMATION: Synthetic Construct

<400> SEQUENCE: 20
gcgcgctact cacggtc                                               17
```